United States Patent
Faltin et al.

(10) Patent No.: US 10,072,258 B2
(45) Date of Patent: Sep. 11, 2018

(54) METHOD AND DEVICE FOR PREPARING A SAMPLE OF BIOLOGICAL MATERIAL CONTAINING TARGET CELLS AND ACCOMPANYING CELLS FOR EXTRACTING NUCLEIC ACIDS OF THE TARGET CELLS

(71) Applicant: Robert Bosch GmbH, Stuttgart (DE)

(72) Inventors: Bernd Faltin, Gerlingen (DE); Franz Laermer, Weil der Stadt (DE); Jochen Rupp, Stuttgart (DE); Peter Rothacher, Bruchsal (DE); Christian Dorrer, Winnenden (DE); Sebastian Berning, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 14/910,530

(22) PCT Filed: Jul. 30, 2014

(86) PCT No.: PCT/EP2014/066362
§ 371 (c)(1),
(2) Date: Feb. 5, 2016

(87) PCT Pub. No.: WO2015/018707
PCT Pub. Date: Feb. 12, 2015

(65) Prior Publication Data
US 2016/0177291 A1 Jun. 23, 2016

(30) Foreign Application Priority Data
Aug. 7, 2013 (DE) .................. 10 2013 215 570

(51) Int. Cl.
*C12N 15/00* (2006.01)
*C12M 1/00* (2006.01)
(Continued)

(52) U.S. Cl.
CPC .......... *C12N 15/1003* (2013.01); *C07H 1/06* (2013.01); *C12M 47/04* (2013.01); *C12M 47/06* (2013.01);
(Continued)

(58) Field of Classification Search
CPC ...... C12N 1/06; C12N 15/1017; C12N 1/066; C12N 15/1003; C07H 1/06; C12M 47/04; C12M 47/06; C12M 1/08
See application file for complete search history.

(56) References Cited

U.S. PATENT DOCUMENTS

| | | | |
|---|---|---|---|
| 4,900,677 A * | 2/1990 | Hewitt | C12N 15/1003 435/259 |
| 8,273,253 B2 * | 9/2012 | Curran | B01L 3/50255 210/384 |

(Continued)

FOREIGN PATENT DOCUMENTS

| | | |
|---|---|---|
| CN | 101405411 A | 4/2009 |
| CN | 101918527 A | 12/2010 |

(Continued)

OTHER PUBLICATIONS

Zhang et al. Synthesis of Novel Porous Magnetic Silica Microspheres as Adsorbents for Isolation of Genomic DNA. Biotechnol. Prog. (2006), v22, p. 514-518.*

(Continued)

*Primary Examiner* — Sean C Barron
(74) *Attorney, Agent, or Firm* — Maginot, Moore & Beck LLP (57) ABSTRACT

A method for preparing a sample of biological materials containing target cells and accompanying cells for extracting nucleic acids of the target cells includes accumulating the target cells of the sample by separating the target cells or the accompanying cells from the sample. The method also (Continued)

includes digesting the target cells via chemical and/or physical lysis in order to produce a target cell lysate containing the nucleic acids of the target cells. The method furthermore includes purifying the nucleic acids from the target cell lysate in order to extract the nucleic acids of the target cells.

7 Claims, 5 Drawing Sheets (51) Int. Cl.
C07H 1/06 (2006.01)
C12N 1/06 (2006.01)
C12N 1/08 (2006.01)
C12N 15/10 (2006.01)
G01N 29/00 (2006.01)

(52) U.S. Cl.
CPC ............... *C12N 1/06* (2013.01); *C12N 1/066* (2013.01); *C12N 1/08* (2013.01); *C12N 15/1017* (2013.01); *G01N 29/00* (2013.01)

(56) References Cited

U.S. PATENT DOCUMENTS

| 2007/0190618 | A1 | 8/2007 | De Witte |
| 2008/0057505 | A1 | 3/2008 | Lin et al. |
| 2010/0285578 | A1* | 11/2010 | Selden ............. B01L 3/502715 435/325 |
| 2012/0190126 | A1* | 7/2012 | Eshoo .................... C12M 47/06 436/174 |

FOREIGN PATENT DOCUMENTS

| DE | 10 2005 009 479 A1 | 9/2006 |
| EP | 1 621 618 A1 | 2/2006 |
| WO | 2008/066858 A2 | 6/2008 |

OTHER PUBLICATIONS

Gaete-Garreton et al. Application of ultrasound in comminution. Ultrasonics (2000), v38, p. 345-352. (Year: 2000).*
International Search Report corresponding to PCT Application No. PCT/EP2014/066362, dated Oct. 16, 2014 (German and English language document) (7 pages).
Chen et al.; Fabrication of DNA extraction device with tethered poly(N-isopropylacrylamide) brushes on silicon surface for a specific DNA detection; Sensors and Actuators B: Chemical; Jun. 2010; pp. 314-320; vol. 150; Elsevier, www.elsevier.com/locate/snb.

* cited by examiner

METHOD AND DEVICE FOR PREPARING A SAMPLE OF BIOLOGICAL MATERIAL CONTAINING TARGET CELLS AND ACCOMPANYING CELLS FOR EXTRACTING NUCLEIC ACIDS OF THE TARGET CELLS

This application is a 35 U.S.C. § 371 National Stage Application of PCT/EP2014/066362, filed on Jul. 30, 2014, which claims the benefit of priority to Serial No. DE 10 2013 215 570.0, filed on Aug. 7, 2013 in Germany, the disclosures of which are incorporated herein by reference in their entirety.

BACKGROUND

The present disclosure relates to a method for processing a sample of biological material containing target cells and accompanying cells for extracting nucleic acids of the target cells and to a device for processing a sample of biological material containing target cells and accompanying cells for extracting nucleic acids of the target cells. The present disclosure concerns in particular the field of microfluidic systems, for example for so-called lab-on-a-chip devices.

In molecular diagnostics, there is often a need to detect pathogenic DNA or RNA in a sample. Pathogenic DNA or RNA refers to the DNA or RNA recovered from a pathogen, for example a virus or a microorganism, for example a bacterium or fungus. The sample is understood to mean in particular a blood sample, but in principle other liquid or liquefied patient samples, for example urine, stool, sputum, cerebrospinal fluid, lavage sample, a rinsed swab or a liquefied tissue sample, can also be meant, particularly when they contain blood or traces of blood. Symptoms in which this is relevant are, for example, urinary tract infections and sepsis. In the event of a suspected urinary tract infection, pathogens are to be detected from urine. In this case, a concentration of the pathogens can be very low, for example $10^3$ to $10^7$ per milliliter. In the event of a suspected sepsis, it is, for example, of interest to detect pathogens from blood and, if necessary, to determine resistances to certain antibiotics. Because of the concentration ratios between pathogens and leukocytes, for example 10 to 1000 per milliliter with respect to $10^6$ to $10^7$ per milliliter, there is in this case a very strong background of human DNA in the sample. Commercially available methods for selectively purifying pathogenic DNA from, for example, blood use, for example, chemical reagents in order to achieve firstly a selective lysis of human cells. Subsequently, the human nucleic acids are enzymatically digested. Pathogens are then isolated, for example by centrifugation and decanting of the supernatant. Such a method is, for example, disclosed in DE102005009479A1.

US 2010/0285578 A1 discloses devices and methods for recovering nucleic acids from biological samples.

SUMMARY

Against this background, the following description presents an improved method for processing a sample of biological material containing target cells and accompanying cells for extracting nucleic acids of the target cells and an improved device for processing a sample of biological material containing target cells and accompanying cells for extracting nucleic acids of the target cells. Advantageous embodiments are revealed by the following description.

According to embodiments of the present disclosure, it is possible to realize a processing of a biological sample particularly for selectively recovering pathogenic nucleic acids from a sample also containing nonpathogenic nucleic acids, for example from blood cells, and/or an accumulation of pathogens from a sample and the subsequent lysis thereof. For example, embodiments of the present disclosure encompass here an approach concerning thermal pretreatment of a sample and/or an approach concerning sample processing using a filter and ultrasound. For instance, what is particularly envisaged is a combination of a thermal pretreatment, in which accompanying cells are selectively lysed, with an enzymatic digestion and a removal by means of filtration with the goal of obtaining target-cell nucleic acids purified from a sample also containing accompanying cells. Also envisaged are, for example, a lysis of bioparticles by means of ultrasound on a filter, it being possible for the compound structure of the filter to be destroyed by ultrasound, and a microfluidic system.

In particular, it is possible to advantageously use embodiments of the present disclosure in systems or laboratory routines used in molecular diagnostics, for example for diagnosing infectious diseases, or for microfluidic lab-on-a-chip systems for molecular diagnostics.

Advantageously, embodiments of the present disclosure make it possible to reliably remove target-cell nucleic acids contained in a sample, for example pathogenic DNA, from a background of accompanying-cell nucleic acids, for example human DNA. This avoids subsequent amplification and detection steps being interfered with by the accompanying-cell nucleic acids, and a detection or diagnostics sensitivity is thus improved. In the case of a thermal pretreatment of a sample, enzymatic digestion in particular can reliably avoid gelling of the sample, which would occur for example when a temperature is too high and/or a pretreatment time is too long. Gelling of the sample can also be avoided here in view of the fact that a gelling-critical temperature and time also depend on properties of the sample such as, for example, the hematocrit. As a result of a, for example, enzymatic digestion, it is possible to avoid the sample clogging a filter. This makes it possible to handle large amounts of sample too. A filtration makes it possible in this case to accumulate only a few pathogens, for example 10 to 1000, from a relatively large blood volume, for example 1 to 10 milliliters. As a result, an effective concentration of target-cell nucleic acids can be increased and a subsequent amplification and detection facilitated or a sensitivity can be increased. Embodiments of the present disclosure are especially well suited for automation, particularly in a microfluidic system. In this case, it is possible to facilitate a procedure and to reduce a risk of contamination.

Thus, embodiments of the present disclosure allow an accumulation of target cells from a sample and thereby increase an efficiency of subsequent amplification and/or detection steps. In this connection, it is also advantageously possible to use in particular ultrasound for lysis of target cells accumulated on a filter, this making it possible to bring about an especially effective disruption. In contrast to, for example, a centrifugation, an accumulation of target cells by means of a filter is very well suited for an automated procedure, for example in a microfluidic system. Such an automated procedure has the advantage that fewer manual operating steps are required and a risk of contamination and/or user errors is reduced. In the case of implementation of embodiments of the present disclosure in a microfluidic system, it is possible to very accurately control flow rates during the accumulation. This makes it possible to avoid a filter being clogged or target cells being accidentally washed through a filter.

A method for processing a sample of biological material containing target cells and accompanying cells for extracting nucleic acids of the target cells has the following steps:

accumulating the target cells of the sample by removing the target cells or the accompanying cells from the sample;

disrupting the target cells by chemical and/or physical lysis in order to generate a target-cell lysate containing the nucleic acids of the target cells; and purifying the nucleic acids from the target-cell lysate in order to extract the nucleic acids of the target cells.

The target cells can encompass pathogenic cells or pathogens, for example viruses or microorganisms, such as, for example, bacteria or fungi, which have DNA and/or RNA as nucleic acids. For the sake of simplicity, nucleic acids will be mentioned frequently hereinafter, with DNA and/or RNA being meant thereby. The accompanying cells can encompass human cells, for example blood cells or the like. A liquid to be analyzed, typically a liquid or liquefied patient sample, for example blood, urine, stool, sputum, cerebrospinal fluid, lavage sample, a rinsed swab or a liquefied tissue sample, can be referred to as sample. In the purification step, the nucleic acids contained in the target-cell lysate can be purified and introduced to a subsequent analysis, by means of which it is possible to verify a presence of certain pathogens or genes, for example resistance genes. Said subsequent analysis can, for example, be achieved by sequencing, polymerase chain reaction (PCR), real-time PCR and/or detection or hybridization on a microarray.

The purification of the target-cell nucleic acids from the sample can be achieved after the disruption or lysis of the target cells by subsequent adsorption of the target-cell nucleic acids to a solid phase, for example a silica filter or microparticles, i.e., so-called beads. Besides chemical and enzymatic methods for lysis, there are also mechanical methods, for example by means of ultrasound or beads. The goal of the purification is to provide the target-cell nucleic acids in concentrated form to an ensuing amplification and/or detection. Embodiments of the present disclosure can be advantageously used also in the case of a removal of the target-cell nucleic acids from cell debris and proteins. Especially human blood samples can, however, additionally contain large amounts of accompanying cells with human DNA. One possibility of removing the target cells from the accompanying cells can consist in firstly selectively disrupting or lysing the accompanying cells, for example blood cells, which are contained in the sample and removing them from the target cells. Thereafter, the target cells can be lysed and the target-cell nucleic acids can be purified. It may be the case that target cells are present in the sample only in a low concentration. In order to concentrate the target cells before purification, the sample can also be, for example, centrifuged or flushed across a filter. Embodiments of the present disclosure make it possible, even in the case of samples containing many accompanying cells, to remove the target-cell nucleic acids from the background of accompanying-cell nucleic acids that is present in the sample. Said accompanying-cell nucleic acids would otherwise interfere with a subsequent amplification and analysis of the target-cell nucleic acids and possibly make it difficult to impossible to detect the presence of the target cells. Thus, it is possible to prevent the accompanying-cell nucleic acids from leading to the formation of undesired secondary products and a lowering of sensitivity in a subsequent amplification and analysis.

In one embodiment, the accumulation step can have a substep of the removal of the target cells from the sample by means of an accumulation filter. In the removal substep, the target cells can be retained by means of an accumulation filter. The advantage of such an embodiment is that an effective and reliable selection of the target cells can be achieved.

In this connection, the accumulation step can have a substep of the cleaning of the accumulation filter after the substep of the removal of the target cells. In this case, the accumulation filter can be washed, for example by water or an aqueous buffer being conducted across the accumulation filter. The advantage of such an embodiment is that miscellaneous constituents of the sample, for example proteins, are rinsed out and the target cells are present in greater purity.

The accumulation step can also have a substep of the temperature adjustment of the sample to a lysis temperature for disrupting the accompanying cells and a substep of the lysis of the accompanying cells by chemical or enzymatic lysis and of the enzymatic digestion of the nucleic acids released from the accompanying cells. In this connection, the temperature-adjustment substep and the lysis and digestion substep can be carried out before the removal substep. The lysis temperature can also be appropriately selected such that the accompanying cells contained in the sample are destroyed or predamaged, with the target cells contained in the sample remaining intact. The advantage of such an embodiment is that an especially effective and reliable selection of the target cells can be achieved. In this connection, the thermal treatment can be used in a specific manner owing to the varying nature of the cell wall. Because of the lysis, it is possible to prevent a clogging during the filtration.

In this connection, the lysis and digestion substep can be carried out before, during or after the temperature-adjustment substep. In this case, a viscosity of the sample can be lowered in the lysis substep. In this connection, temperature-resistant enzymes in particular can be used in the lysis and digestion substep. The advantage of such an embodiment is that this can reliably prevent a gelling of the sample even during the thermal pretreatment.

Furthermore, the target cells can be disrupted in the disruption step by coupling-in of ultrasound. The advantage of such an embodiment is that ultrasound-elicited pressure waves and cavitation lead to cell walls of the target cells being especially reliably and rapidly destroyed.

In the disruption step, the target cells can be disrupted on a filter and, in the course of this, the compound structure of the filter can be completely or partially destroyed or the filter can be completely or partially broken up into its constituents. The filter can be the aforementioned accumulation filter.

It is also possible to envisage a step of the predisruption of the accompanying cells by means of a lysis buffer and, additionally or alternatively, coupling-in of ultrasound before the accumulation step. In this connection, it is possible in the predisruption step to bring about a gentle lysis of the sample, in which accompanying cells contained in the sample are selectively lysed, whereas the target cells remain intact. The advantage of such an embodiment is that the accompanying-cell nucleic acids are already released in said step and not concomitantly accumulated. The gentle lysis in the predisruption step can, for example, be achieved by a mild enzymatic or chemical lysis. Alternatively, the gentle lysis can also be achieved by treatment of the sample with ultrasound of low energy. This has the advantage that no or fewer additional reagents need to be added. The treatment of the sample with ultrasound also shreds the nucleic acids released from the accompanying cells, improving the handleability of the sample. Thus, the sample can be conducted across the accumulation filter with lower pressure and a clogging of the accumulation filter can be avoided.

Moreover, the accumulation step can have a substep of the dilution of the sample. In this case, the sample can be diluted with water, an aqueous buffer and/or an oil, for example a silicone oil. The advantage of such an embodiment is that a viscosity of the sample is lowered, improving a handleability of the sample. Thus, the sample can be conducted across the accumulation filter with lower pressure and a clogging of the accumulation filter can be avoided. If the accumulation step has the substep of the temperature adjustment of the sample, the dilution substep can be carried out before or after the temperature-adjustment substep. In this way, it is, on the one hand, possible to avoid even more reliably a gelling during the thermal treatment or it is, on the other hand, also possible by osmotic shock to effectively further lyse accompanying cells which were predamaged during the thermal treatment.

A device for processing a sample of biological material containing target cells and accompanying cells for extracting nucleic acids of the target cells has the following features:
a unit for accumulating the target cells of the sample by removing the target cells or the accompanying cells from the sample;
a unit for disrupting the target cells by chemical and/or physical lysis in order to generate a target-cell lysate containing the nucleic acids of the target cells; and
a unit for purifying the nucleic acids from the target-cell lysate in order to extract the nucleic acids of the target cells.

The aforementioned processing device can be advantageously used or utilized in conjunction with any embodiment of the processing method in order to process a sample of biological material containing target cells and accompanying cells in order to be able to extract nucleic acids of the target cells. The device is designed to carry out or implement the steps of the processing method in corresponding units. This variant of the disclosure in the form of a device, too, can rapidly and efficiently achieve the object of the disclosure. The device can be in the form of a microfluidic system, particularly for a so-called lab-on-a-chip.

In one embodiment, the accumulation unit can have an accumulation filter for removing the target cells from the sample. The advantage of such an embodiment is that an effective and reliable selection of the target cells is achieved.

In particular, it is possible for the accumulation filter of the accumulation unit to be also used by the disruption unit and, additionally or alternatively, the purification unit. The advantage of such an embodiment is that a filter is saved when the target cells are lysed on the accumulation filter and the accumulation filter is also used for DNA purification. In order to realize this, a lysis buffer used for disruption can be adjusted such that target-cell nucleic acids released upon disruption bind directly to the accumulation filter. Alternatively, it is possible following the disruption to add a binding buffer to the accumulation filter, without displacing the lysis buffer from the accumulation filter. In this case, a mix of lysis buffer and binding buffer in the accumulation filter can be achieved by means of diffusion. Alternatively, it is possible for the binding buffer to be fed through the filter against the initial flow direction and mixed with the lysis buffer.

The accumulation unit can also have temperature-adjustment means for adjusting the temperature of the sample to a lysis temperature for disrupting or predamaging the accompanying cells. Furthermore, the accumulation unit can have a supply chamber for a buffer solution for lysing the accompanying cells by chemical lysis. In this case, the temperature-adjustment means can have a heating unit or a heating unit and a cooling unit. The temperature-adjustment means can also be designed for heating and/or for cooling. The advantage of such an embodiment is that an especially effective and reliable selection of the target cells is achieved. In this connection, the thermal treatment can be used in a specific manner owing to the varying nature of the cell wall. Because of the lysis, it is possible to prevent a clogging during the filtration. In particular, the temperature-adjustment means can accurately set the lysis temperature. If the temperature-adjustment means also have a cooling unit, the sample can be brought to a second defined temperature level, for example room temperature, before the lysis, and so it is possible to especially accurately set a thermal pretreatment time and it is also possible to especially reliably avoid a gelling of the sample.

In this connection, the temperature-adjustment means can be thermally coupled with a sample chamber or a sample channel arranged between a sample chamber and a disruption chamber. The advantage of such an embodiment is that the thermal treatment of the sample can, depending on the application, be achieved in a stationary manner or on the basis of flow-through.

In one embodiment, the disruption unit can have an ultrasound coupling-in unit arranged adjacently to the accumulation unit. In this connection, the ultrasound coupling-in unit can have an ultrasonic sonotrode. The advantage of such an embodiment is that ultrasound-elicited pressure waves and cavitation lead to cell walls of the target cells being especially reliably and rapidly destroyed.

In particular, the accumulation filter can be designed to be completely or partially broken into fragments or particles or broken up into its constituents by coupling-in of ultrasound. This can, for example, be achieved in the disruption step mentioned. In this case, the accumulation filter can have in particular a filter composed of inorganic fibers or particles, for example composed of aluminum oxide or silica, a porous membrane or a membrane having defined holes. The accumulation filter is also designed to retain, on the basis of their size, target cells contained in the sample. Ultrasound-elicited pressure waves and shearing forces lead firstly to a destruction of the cell walls of the target cells, and secondly to an, at least partial, destruction of the compound structure of the accumulation filter. For example, a fiber filter is broken up into individual fibers. A packed silica filter is correspondingly broken up into silica particles. The advantage of such an embodiment is that the target cells remain bound in part to the filter particles, and this yet further improves the lysis properties owing to particle collisions. As a result, it is possible to reduce the ultrasound intensity, and this also has the advantage of a lower fragmentation of released target-cell nucleic acids.

In this connection, the accumulation filter can be only partially broken up. The liberated fragments or constituents of the filter are then collected by the still intact regions of the filter in the further course of processing or are packed together again to form a secondary filter in front of the still intact regions of the accumulation filter. By adding a binding buffer, it is moreover possible to set the chemical conditions such that target-cell nucleic acids released during the disruption are adsorbed on said secondary filter and possibly the further filter, whereas miscellaneous constituents, for example proteins and cell debris, are rinsed out.

Alternatively, the purification unit can have a further filter arranged downstream of the accumulation filter. In this case, the further filter can be designed to collect the fragments or particles of the accumulation filter or to remove them from the target cells or the lysis products thereof. The advantage of such an embodiment is that the ultrasound-liberated constituents of the accumulation filter are retained on the further filter and are packed to form a secondary filter in front of the further filter.

The disclosure will be more particularly elucidated by way of example on the basis of the attached drawings.

DETAILED DESCRIPTION

In the following description of preferred exemplary embodiments of the present disclosure, identical or similar reference signs are used for the elements shown in the various figures and acting in a similar manner, and a repeated description of said elements is dispensed with.

Figure 1:
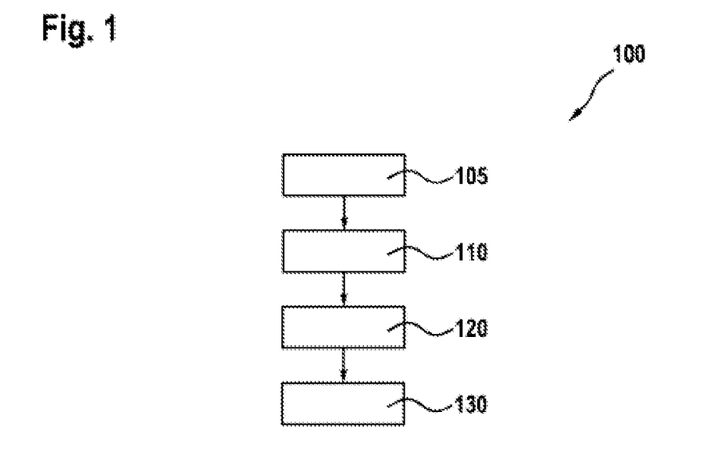
FIG. 1 shows a flowchart of a processing method according to one exemplary embodiment of the present disclosure.

FIG. 1 shows a flowchart of a method 100 for processing a sample of biological material containing target cells and accompanying cells for extracting nucleic acids of the target cells according to one exemplary embodiment of the present disclosure. It is advantageously possible to carry out the processing method 100 in conjunction with a device, such as the processing device from any of FIGS. 2 to 9. In said flowchart, the method 100 has a step 105 of the predisruption of the accompanying cells and, optionally, of the digestion of the nucleic acids released from the accompanying cells by means of a lysis buffer and, additionally or alternatively, coupling-in of ultrasound. The method 100 has a step 110 of the accumulation of the target cells of the sample by removing the target cells or the accompanying cells from the sample. The method 100 also has a step 120 of the disruption of the target cells by chemical lysis and, additionally or alternatively, by physical lysis in order to generate a target-cell lysate containing the nucleic acids of the target cells. Furthermore, the method 100 has a step 130 of the purification of the nucleic acids from the target-cell lysate in order to extract the nucleic acids of the target cells.

In one exemplary embodiment, the predisruption step 105 is optionally carried out or skipped. In this case, the method 100 has the accumulation step 110, the disruption step 120 and the purification step 130.

In one exemplary embodiment, the accumulation step 110 has a substep of the removal of the target cells from the sample by means of an accumulation filter. In this case, in one exemplary embodiment, the accumulation step 110 has a substep of the cleaning of the accumulation filter after the substep of the removal of the target cells.

In one exemplary embodiment, the accumulation step 110 has a substep of the temperature adjustment of the sample to a lysis temperature for disrupting the accompanying cells and a substep of the lysis of the accompanying cells by chemical lysis. In this case, in one exemplary embodiment, the lysis and digestion substep is carried out before, during or after the temperature-adjustment substep, a viscosity of the sample being lowered in the lysis and digestion substep.

In one exemplary embodiment, the accumulation step 110 has a substep of the dilution of the sample.

In one exemplary embodiment, the target cells are disrupted in the disruption step 120 by coupling-in of ultrasound.

Figure 2:
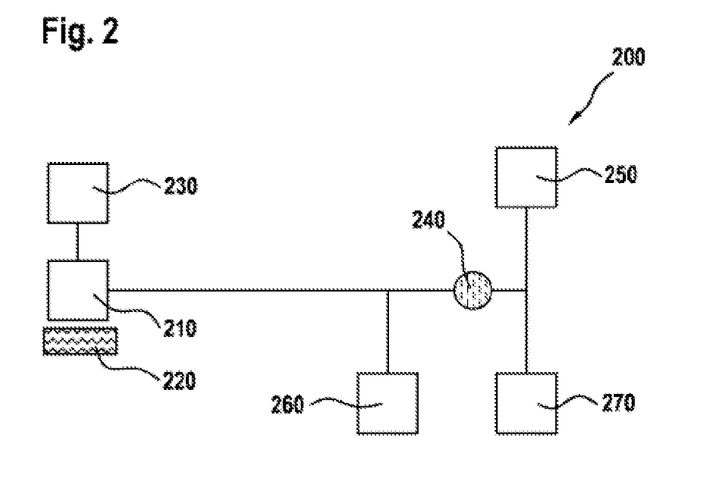
FIGS. 2 to 9 show processing devices according to exemplary embodiments of the present disclosure.

FIG. 2 shows a device 200 for processing a sample of biological material containing target cells and accompanying cells for extracting nucleic acids of the target cells according to one exemplary embodiment of the present disclosure. In this case, the device 200 is implemented as a microfluidic system or part of a microfluidic system. What is shown here of the device 200 are a sample chamber 210, a temperature-adjustment unit in the form of a heater 220, a supply chamber 230 for a first buffer, a filter 240, a waste chamber 250, a lysis buffer supply chamber 260 and a collection chamber 270.

The heater 220 is arranged adjacently to the sample chamber 210. In this case, the heater 220 is thermally coupled with the sample chamber 210. The supply chamber 230 is connected to the sample chamber 210 by means of a fluid connection. The filter 240 is arranged between the sample chamber 210, on the one hand, and the waste chamber 250 and the collection chamber 270, on the other. Here, the sample chamber 210 is connected to the waste chamber 250 and the collection chamber 270 by means of a fluid connection across the filter 240. The lysis buffer supply chamber 260 is connected in a fluid-conducting manner to a fluid connection between the sample chamber 210 and the filter 240.

The sample chamber 210 has a resealable opening, for example by means of a stopper, lid or adhesive film, for introducing the sample. The heater 220 is, for example, a Peltier heater or resistance heater. The waste chamber 250 serves to accommodate filtrate. The collection chamber 270 serves to accommodate lysate.

Thus, FIG. 2 shows a topology of the device 100 or of a microfluidic system in which a thermal treatment of the sample is carried out in the sample chamber 210 in a stationary manner. An operation of the device 200 will be discussed further below.

Figure 3:
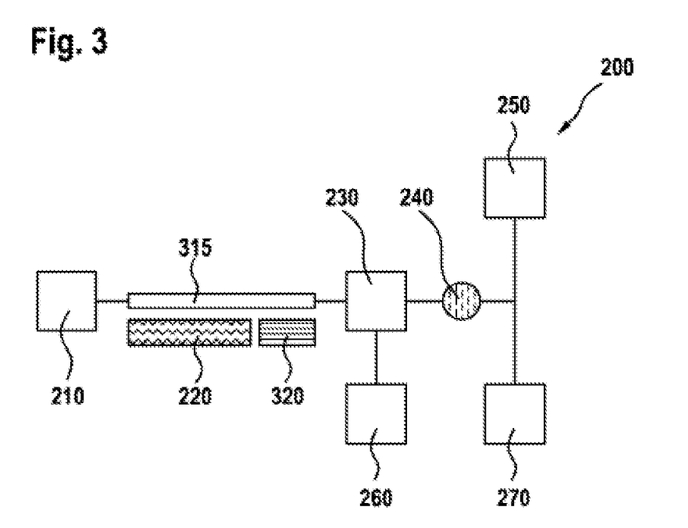

FIG. 3 shows a device 200 for processing a sample of biological material containing target cells and accompanying cells for extracting nucleic acids of the target cells according to one exemplary embodiment of the present disclosure. The device 200 is similar to the device from FIG. 2. What is shown here of the device 200 are the sample chamber 210, the heater 220, the supply chamber 230 for the first buffer, the filter 240, the waste chamber 250, the lysis buffer supply chamber 260, the collection chamber 270, a microchannel 315 and a cooler 320.

The microchannel 315 is arranged between the sample chamber 210 and the supply chamber 230. The sample chamber 210 is connected to the supply chamber 230 by means of a fluid connection across the microchannel 315. The heater 220 and the cooler 320 form the temperature-adjustment unit. In this case, the heater 220 and the cooler 320 are arranged adjacently to the microchannel 315. The heater 220 and the cooler 320 are thermally coupled with the microchannel 315. The supply chamber 230 is arranged here between the microchannel 315 and the filter 240. The filter 240 is arranged between the supply chamber 230, on the one hand, and the waste chamber 250 and the collection chamber 270, on the other. The lysis buffer supply chamber 260 is connected to the supply chamber 230 by means of a fluid connection.

Thus, FIG. 3 shows a topology of the device 200 for carrying out a thermal treatment in flow-through mode. In this case, the sample is pumped from the sample chamber 210 through the temperature-adjustable microchannel 315 into the supply chamber 230, in which the first buffer is situated. The temperature-adjustable microchannel 315 is heatable by means of the heater 220 and, if necessary, coolable by means of the cooler 320, for example a Peltier cooler. The cooler 320 as second thermally active element makes it possible to adjust the temperature of the heated sample to a defined temperature level, for example room temperature, before a mixing with the first buffer. This has the advantage that it is possible to especially accurately set a thermal pretreatment time and it is thus possible to especially reliably avoid a gelling of the sample. An operation of the device 200 will be discussed in more detail further below.

Figure 4:
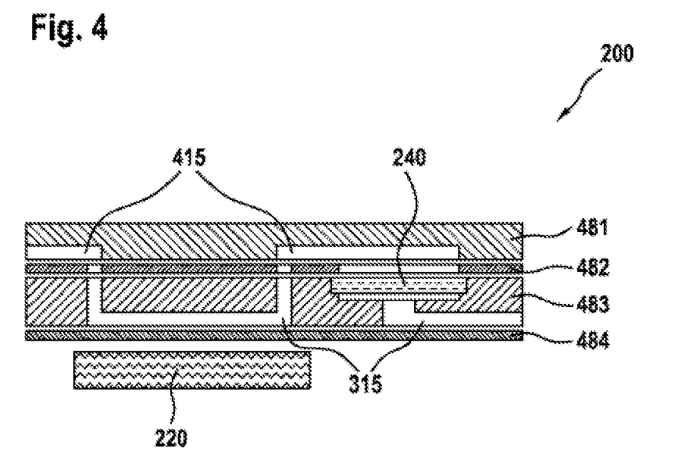

FIG. 4 shows a device 200 for processing a sample of biological material containing target cells and accompanying cells for extracting nucleic acids of the target cells according to one exemplary embodiment of the present disclosure. The device 200 is similar to the device from FIG. 3, though in FIG. 4 the device 200 is shown in a sectional view in a multilayer structure design, with the chambers of the device 200 being omitted in the picture. What is shown here of the device 200 are the heater 220, the filter 240, the microchannel 315, a further microchannel 415, a first structured polymeric layer 481, a polymeric film 482, a second structured polymeric layer 483 and a polymeric lid film 484.

The structured polymeric layers 481 and 483 are, for example, formed from thermoplastic polymers, for example PP, PC, PE, PS, COP, COC, etc. The polymeric film 482 is, for example, formed from thermoplastic polymers, thermoplastic elastomers, elastomers or the like. The lid film 484 has, for example, a thermoplastic film, adhesive film or the like.

The further microchannel 415 extends between the temperature-adjustable microchannel 315 and the filter 240. The first structured polymeric layer 481, the polymeric film 482, the second structured polymeric layer 483 and the polymeric lid film 484 represent the multilayer structure of the device 200 according to the exemplary embodiment of the present disclosure that is shown in FIG. 4. The advantage of such a design is that it is manufacturable in a cost-effective manner and, by means of the polymeric film 482, it is also possible to realize active elements such as valves. Furthermore, an advantage of this exemplary embodiment of the present disclosure is that the temperature-adjustable microchannel 315 is separated from the heater 220 merely by the thin lid film 484. As a result, it is possible to especially accurately set a temperature in the temperature-adjustable microchannel 315. An operation of the device 200 will be discussed in more detail further below.

Figure 5:
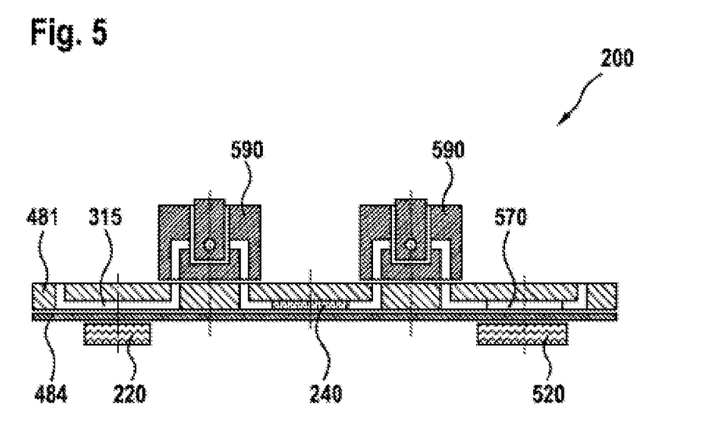

FIG. 5 shows a device 200 for processing a sample of biological material containing target cells and accompanying cells for extracting nucleic acids of the target cells according to one exemplary embodiment of the present disclosure. The device 200 is similar to the device from FIG. 4. What is shown here of the device 200 are the heater 220, the filter 240, the microchannel 315, the first structured polymeric layer 481, the polymeric lid film 484, a further heater 520, a heatable amplification chamber 570 and, by way of example, two rotary valves 590.

In this case, the first structured polymeric layer 481 and the polymeric lid film 484 represent the multilayer structure of the device 200 according to the exemplary embodiment of the present disclosure that is shown in FIG. 5. The first of the rotary valves 590 is arranged between the microchannel 315 and the filter 240 and designed to unblock or to block a fluid connection between them. The second of the rotary valves 590 is arranged between the filter 240 and the amplification chamber 570 and designed to unblock or to block a fluid connection between them. The further heater 520 is arranged adjacently to the amplification chamber 570 and thermally coupled with it. Therefore, the filter 240 is arranged between the two rotary valves 590.

Thus, FIG. 5 shows a design of the device 200 in the form of a multilayer structure with merely two layers. The advantage of such a design is that the device 200 is manufacturable in an especially cost-effective manner. The liquids are controlled here by means of the rotary valves 590. Furthermore, such a design has the additional amplification chamber 570 which is heatable by means of the further heater 520 and in which, after a purification of the target-cell nucleic acids, an amplification thereof can be carried out by means of PCR.

Hereinafter, an approach concerning thermal pretreatment of a sample using the method 100 and the device 200 according to exemplary embodiments of the present disclosure will be explained with reference to FIGS. 1 to 5.

In the accumulation step 110, in one exemplary embodiment, the actual thermal pretreatment of the sample is carried out in a first substep. In this case, the sample is heated to, for example, a temperature or lysis temperature between 60 and 90 degrees Celsius, more particularly between 65 and 85 degrees Celsius. The temperature is in this case adjusted such that the accompanying cells contained in the sample, for example blood cells such as leukocytes, are destroyed or predamaged and the nucleic acids contained in the accompanying cells, i.e., human DNA, are at least partly released, but the target cells contained in the sample, for example pathogens, remain intact. Such a selective lysis of the accompanying cells is possible because the target cells, as pathogens, have a more robust cell wall and are thereby more stable with respect to thermal stresses. The heating of the sample can, for example, be done in a stationary manner in one of the sample chambers 210 or in flow-through mode in a capillary, a piece of tubing or a channel such as the microchannel 315. The liquid arising in this substep is referred to as first lysate.

In the accumulation step 110, a mixing of the first lysate with a first buffer containing enzymes, for example proteases, DNAses and lysozyme, from the supply chamber 230 is then carried out in a second substep. Said first buffer brings about a digestion or a shredding of the damaged cells, cell debris, proteins and nucleic acids of the accompanying cells that arise or are released in the first substep. Said digestion is essential for a subsequent filtration substep, since a gelling of the first lysate is avoided, the viscosity of the first lysate is lowered and thus a clogging of the filter 240 is prevented. Also, a removal of still intact cellular constituents of the first lysate is achieved more easily in the filtration. The liquid arising in this substep is referred to as digested lysate.

In the accumulation step 110, the filtration is then carried out in a third substep, with the digested lysate being conducted across the filter 240, for example a sterile, fibrous or silica filter. Still intact cellular constituents, more particularly the target cells, are retained and thus accumulated on the filter 240 owing to their size.

In one exemplary embodiment, the sample is diluted with an aqueous buffer, for example in a ratio between 1:1 and 1:10, before the first substep of the accumulation step 110. The advantage of this is that the viscosity of the sample is lowered and a gelling is even more reliably avoided during the thermal treatment. If necessary, the dilution with the aqueous buffer can also be carried out after the first substep of the accumulation step 110. The advantage of this is that, owing to the osmotic shock triggered as a result, accompanying cells which were only predamaged in the first substep are effectively lysed too.

In one exemplary embodiment, further components are added in the second substep of the accumulation step 110, for example detergents, such as, for example, saponins, SDS or the like, chaotropic salts or basic components, such as, for example, NaOH. The advantage of this is that, also, accompanying cells which were only predamaged in the first substep of the accumulation step 110 are efficiently lysed and the nucleic acids thereof are released.

In one exemplary embodiment, the first substep of the accumulation step 110 is carried out after the second substep of the accumulation step 110. As a result, a gelling of the sample is reliably avoided even during the thermal pretreatment. In this case, temperature-resistant enzymes are used in the first buffer.

In one exemplary embodiment, the target cells, instead of being lysed on the filter 240 in the disruption step 120, are flushed away from the filter 240 before the mixing with the lysis buffer, for example by a buffer, for example an aqueous buffer, being flushed across the filter 240 in the opposite direction.

In one exemplary embodiment, the filter 240, if the target cells are being lysed on the filter 240 in the disruption step 120, is advantageously also directly used in the purification step 130. The advantage of this is that a filter is saved. In order to realize this, the lysis buffer can be adjusted such that target-cell nucleic acids released in the disruption step 120 bind directly to the filter 240. Alternatively, it is possible following the disruption step 120 to add a binding buffer to the filter 240, without displacing the lysis buffer from the filter 240. The mixing of lysis buffer and binding buffer in the filter 240 is then achieved by means of diffusion.

In one exemplary embodiment, the digested lysate is also heated or treated with ultrasound during the disruption step 120. A thermal stress or ultrasound-elicited pressure waves and cavitation lead to the cell walls of the target cells being especially reliably and rapidly destroyed.

A possible further procedure for processing the sample of biological material containing target cells and accompanying cells for extracting nucleic acids of the target cells will be described below.

In the disruption step 120, the target cells are lysed. This gives rise to a second lysate. The lysis or the disruption is achieved by adding the lysis buffer from the lysis buffer supply chamber 260 to the filter 240. Said lysis buffer can, for example, contain enzymes, for example proteinase K, proteases and lysozyme. These enzymes bring about a destruction of the cell wall of the target cells and thus a release of the target-cell nucleic acids. The cell wall of the target cells can also be destroyed in another way, for example by addition of chemical reagents, for example chaotropic salts, detergents such as, for example, saponins, SDS or the like, β-mercaptoethanol or basic components such as, for example, NaOH.

In the purification step 130, the target-cell nucleic acids are purified from the second lysate, for example by adsorption to a solid phase.

Typically, the purification step 130 is followed by an analysis of the target-cell nucleic acids. The aim of said analysis can be, for example, to detect a presence of certain pathogens and resistance genes. Typically, the target-cell nucleic acids are firstly selectively amplified for this purpose, for example by means of a PCR. In the PCR, addition of a PCR master mix and repeated initiation of different temperature levels achieve an exponential increase in the nucleic acid amount. The PCR master mix typically contains a buffer solution, nucleotides, polymerase, primers, magnesium chloride and optionally bovine serum albumin (BSA). This is followed by, for example, a detection of the amplified target-cell nucleic acids by means of hybridization on a microarray.

An advantage in the realization of the approach concerning processing in a microfluidic system using a thermal pretreatment of the sample is that the method 100 can be carried out in a microfluidic system in an especially defined and reproducible manner, since the temperatures, the volumes and, when carrying out the method in flow-through mode, the flow rates can be especially accurately set. Furthermore, it is possible to minimize a risk of a contamination of the sample from the outside or of the environment by the sample, since the method 100 is carried out in the device 200 as a closed system.

Figure 6:
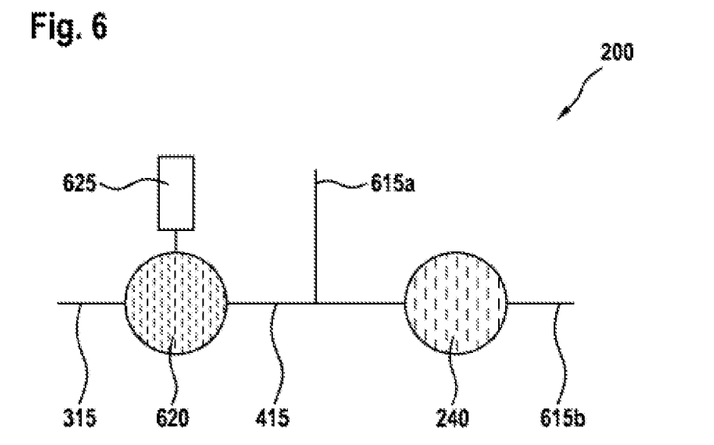

FIG. 6 shows a device 200 for processing a sample of biological material containing target cells and accompanying cells for extracting nucleic acids of the target cells according to one exemplary embodiment of the present disclosure. In this case, the device 200 is implemented as a microfluidic system or part of a microfluidic system. The device 200 is similar to the device from any of FIGS. 2 to 5. What is shown here of the device 200 are the filter 240 or a screen, the microchannel 315 as inlet channel, the further microchannel 415 as connecting channel, a first outlet channel 615a, a second outlet channel 615b, a second filter 620 and an ultrasonic sonotrode 625.

The ultrasonic sonotrode 625 is arranged adjacently to the filter 240. In this case, the ultrasonic sonotrode 625 is designed to couple in ultrasonic waves into a region of the filter 240. The filter 240 is arranged between the microchannel 315 or inlet channel and the further microchannel 415 or connecting channel. The filter 240 is designed to be completely or partially comminuted into fragments or particles by the ultrasonic waves coupled in by means of the ultrasonic sonotrode 625. The further microchannel 415 extends between the filter 240 and the second filter 620 or screen. The first outlet channel 615a branches away from the further microchannel 415. The second filter 620 is arranged between the further microchannel 415 and the second outlet channel 615b.

The sample is flushed through the inlet channel or microchannel 315, across the filter 240 and the connecting channel or further microchannel 415, into the first outlet channel 615a. Filter 240 is then treated with ultrasound. Thereafter, the lysate is flushed across the further microchannel 415 and the second filter 620 into the second outlet channel 615b. An operation of the device 200 will be discussed in more detail further below.

Figure 7:
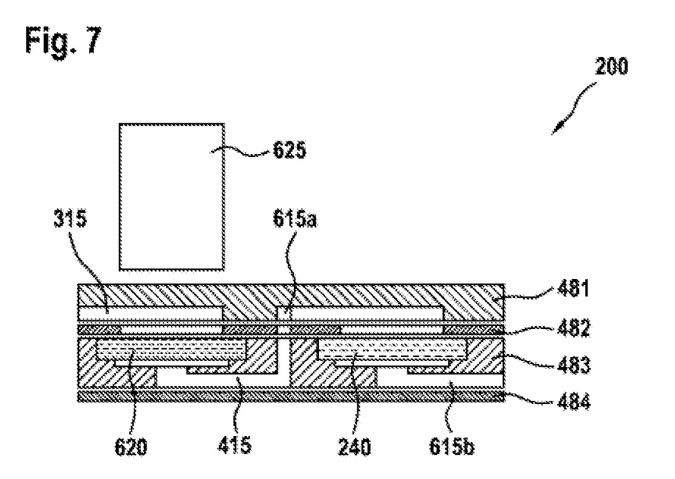

FIG. 7 shows a device 200 for processing a sample of biological material containing target cells and accompanying cells for extracting nucleic acids of the target cells according to one exemplary embodiment of the present disclosure. The device 200 corresponds to the device from FIG. 6, though in FIG. 7 the device 200 is shown in a sectional view, similar to FIG. 4, in a multilayer structure design. What is shown here of the device 200 are the filter 240, the microchannel 315 as inlet channel, the further microchannel 415 as connecting channel, the first structured polymeric plate or polymeric layer 481, the polymeric membrane or polymeric film 482, the second structured polymeric plate or polymeric layer 483, the lid film 484, the first outlet channel 615a, the second outlet channel 615b, the second filter 620 and the ultrasonic sonotrode 625.

The first structured polymeric layer 481, the polymeric film 482, the second structured polymeric layer 483 and the lid film 484 represent the multilayer structure of the device 200 according to the exemplary embodiment of the present disclosure that is shown in FIG. 7. The advantage of such a design of the device 200 is that it is manufacturable in a cost-effective manner. The multilayer structure can, for example, be joined by welding, for example laser-beam welding, adhesive bonding or clamping by means of rivets. The structured polymeric layers 481 and 483 are, for example, formed from thermoplastic polymers, for example PP, PC, PE, PS, COP, COC, etc. The polymeric membrane or polymeric film 482 is, for example, formed from thermoplastic polymers, thermoplastic elastomers, elastomers or the like. The lid film 484 has, for example, a thermoplastic film, adhesive film or the like.

Figure 8:
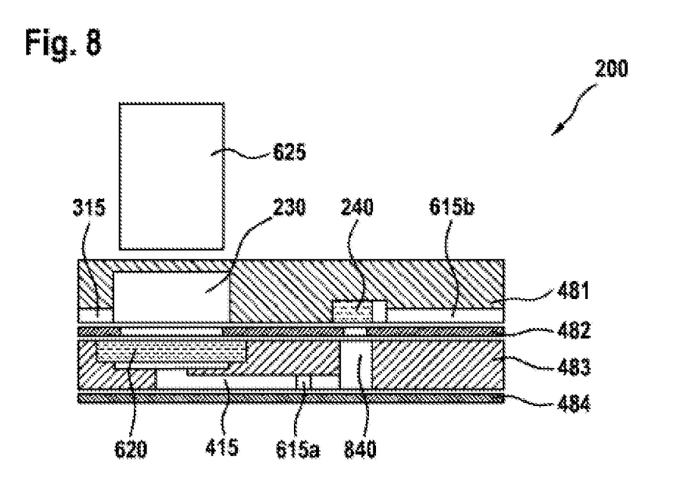

FIG. 8 shows a device 200 for processing a sample of biological material containing target cells and accompanying cells for extracting nucleic acids of the target cells according to one exemplary embodiment of the present disclosure. The device 200 corresponds to the device from FIG. 7, with the exception that the inlet channel or microchannel 315 is expanded in the region of the ultrasonic sonotrode 625 to form the lysis chamber 230 and that the filter or the screen 240 receives flow across a smaller cross section than the prefilter 620, and in a region in front of the second filter 620 or screen an elongated cavity 840 is formed in which the constituents of the filter 240 can be collected and form a packed secondary filter.

The inlet channel or microchannel 315 is expanded in the region of the filter 240 to form the lysis chamber 230, the typical volume of which is between 100 microliters and 3 milliliters and typically 1 milliliter. The advantage of this is that a gentle lysis can be carried out by means of ultrasound in the lysis chamber 230, without a further ultrasonic sonotrode being required. The second filter 620 or the screen receives flow across a smaller cross section than the filter 240. Formed in the region in front of the second filter 620 or screen is the elongated cavity 840, in which the constituents of the filter 240 can be collected and form the packed secondary filter. The advantage of this is that a smaller volume can be used for eluting the target-cell nucleic acids, and so the nucleic acid concentration in the eluate is increased. In the exemplary embodiment of the present disclosure that is shown in FIG. 8, the elongated cavity 840 is implemented as a breach through the second structured polymeric layer 483.

Figure 9:
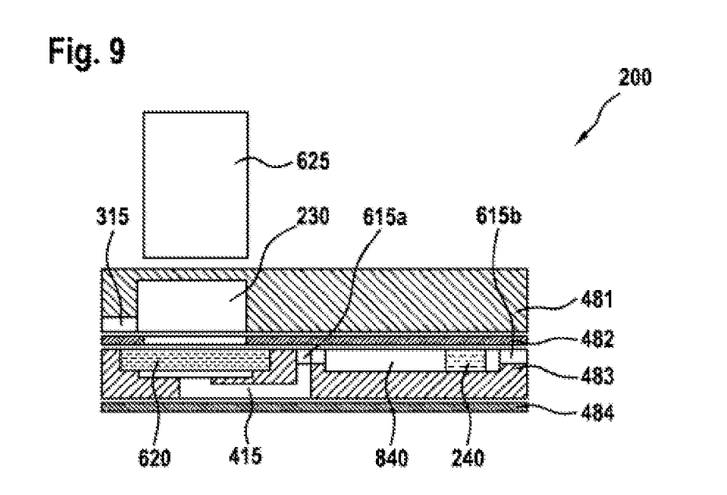

FIG. 9 shows a device 200 for processing a sample of biological material containing target cells and accompanying cells for extracting nucleic acids of the target cells according to one exemplary embodiment of the present disclosure. The device 200 corresponds to the device from FIG. 8, with the exception that the elongated cavity 840 according to the exemplary embodiment of the present disclosure that is shown in FIG. 9 is implemented as a channel running in the second structured polymeric layer 483.

Hereinafter, an approach concerning sample processing with a filter using the method 100 and the device 200 according to exemplary embodiments of the present disclosure will be explained with reference to FIGS. 1 and 6 to 9. As a result of ultrasonic action and destruction of the compound structure of the filter 240, the target cells bound therein are transferred back into the liquid phase, where an ultrasonic lysis is especially effective. In this case, the target cells remain bound in part to filter particles, and this yet further improves the lysis properties owing to particle collisions. As a result, the ultrasound intensity can be possibly lowered below the cavitation threshold or the ultrasound frequency can be raised, for example by severalfold, for example doubled, such that cavitation no longer occurs without losing the lysis properties. The reduced ultrasound intensity and extensive lack of cavitation has the advantage of a lower fragmentation of released target-cell nucleic acids. The nucleic acids released in this case can immediately pass into the solution.

In the accumulation step 110, the sample is conducted across the filter 240, which is, for example, a filter composed of inorganic fibers or particles, for example composed of aluminum oxide or silica, a porous membrane or a membrane having defined holes. Target cells contained in the sample are retained on the filter 240 owing to their size. The sample is, for example, conducted across the filter 240 using a pump, for example a peristaltic pump or a diaphragm pump, or by means of centrifugation.

In the disruption or lysis step 120, the filter 240 is treated with ultrasound, for example at a frequency of 20 to 50 kilohertz. The ultrasound-generated pressure waves and shear forces lead firstly to the destruction of the cell walls of the target cells and secondly to a complete or partial destruction of the compound structure of the filter 240. The filter particles of the filter 240 support a lysis effect. For example, a fabric filter is broken up into individual threads. A packed silica filter is correspondingly broken up into silica particles. The liquid or suspension arising in the disruption step 120 is referred to as lysate. Advantageously, cavitation is generated by the ultrasound. The advantage of this is that the pressure waves and shear forces which occur are especially high. Furthermore, it is possible to firstly break up the silica filter as filter 240 with a few intense ultrasonic pulses via cavitation effects and to transfer at least superficial silica particles with target cells bound thereto, as suspension, back into the solution, with firstly only a few target cells needing to be lysed. In a next substep of the disruption step 120, the actual lysis is carried out with ultrasound of lower intensity below the cavitation threshold, with the silica particles from the filter material of the filter 240 acting in a supporting manner. Such lysis conditions have been found to be especially favorable for the attainment of highly unfragmented nucleic acids from the lysed target cells. Advantageously, the filter 240 is filled with liquid in this step. The advantage of this is that the ultrasound energy is coupled in an especially good and defined manner.

In the purification step 130, a filtration is carried out, with the lysate being mixed with a binding buffer, for example an ethanol-containing binding buffer, and conducted across the second filter 620 or the screen. The constituents of the filter 240 are retained on the second filter 620 and are packed in front of the second filter 620 to form a so-called secondary filter. As a result of the addition of the binding buffer, the chemical conditions in this step are adjusted such that target-cell nucleic acids released in the lysis are adsorbed on said secondary filter and possibly the second filter 620 or screen, whereas miscellaneous constituents, for example proteins and cell debris, are rinsed out. The lysate mixed with binding buffer can, for example, be conducted across the second filter 620 or the screen using a pump, for example a peristaltic pump or a diaphragm pump, or by means of centrifugation.

A possible further procedure for processing the sample of biological material containing target cells and accompanying cells for extracting the nucleic acids of the target cells will be described below. The nucleic acids adsorbed on the secondary filter and the second filter 620 are washed and eluted. The advantage of this is that purity and concentration of the nucleic acids are increased. The step 130 of the purification of the target-cell nucleic acids can be followed by an amplification and/or detection, for example by means of sequencing, polymerase chain reaction (PCR), real-time PCR and/or hybridization on a microarray.

In one exemplary embodiment, a so-called gentle lysis is carried out in step 105 before the accumulation step 110. Gentle lysis refers to a step in which accompanying cells contained in the sample, more particularly blood cells in the case of the presence of a blood sample, are selectively lysed, whereas the target cells remain intact. The advantage of this is that the accompanying-cell nucleic acids are already released in said step and not concomitantly accumulated. The gentle lysis can, for example, be achieved by a mild enzymatic or chemical lysis. For this purpose, the sample is admixed with, for example, reagents, for example enzymes, for example proteases, lysozyme and DNAses, basic components, for example NaOH, detergents, for example SDS, or chaotropic salts. In particular, the advantage of the addition of DNAses is that the nucleic acids released in this first, gentle lysis step are digested and thus especially effectively removed. Alternatively or additionally, the gentle lysis and the digestion of the nucleic acids released in the gentle lysis step can also be achieved by treating the sample with ultrasound of reduced energy. The advantage of this is that no or fewer additional reagents need to be added.

In one exemplary embodiment, water or an aqueous buffer is added to the sample before the accumulation step 110. The advantage of this is that the sample is diluted and can therefore be conducted more easily, i.e., with lower pressure, across the prefilter 620 and a clogging of the prefilter 620 is avoided.

In one exemplary embodiment, the filter 240 is washed after the accumulation step 110, for example by water or an aqueous buffer being conducted across the filter 240. The advantage of this is that miscellaneous constituents of the sample, for example proteins, are rinsed out and the target cells are present in a greater purity.

In one exemplary embodiment, the addition of a binding buffer in the purification step 130 is omitted. In this case, the filtrate which arises in the purification step 130 and which, in this case, contains the target-cell nucleic acids will be further processed. The advantage of this is that any other method can be used for the further processing.

In one exemplary embodiment, a buffer containing proteinase K is additionally added in the purification step 130 before addition of the binding buffer. The advantage of this is that cell debris is shredded and can therefore be rinsed out especially well.

In one further exemplary embodiment, the second filter 620 is omitted. It has become apparent that the ultrasound parameters can be adjusted or the ultrasound energy can be minimized such that the ultrasound treatment breaks up or comminutes the filter 240 only superficially, rather than completely, into its constituents. The ultrasound-treated filter 240 can thus be used further as filter. In following process steps, the particles arising as a result of the ultrasound treatment are collected and retained by the still intact subregions of the filter 240.

The exemplary embodiments which are described and are shown in the figures have been selected only by way of example. Different exemplary embodiments can be combined with one another in full or with respect to individual features. It is also possible for one exemplary embodiment to be supplemented by features of a further exemplary embodiment. Furthermore, method steps can be repeated and carried out in a sequence different to the one described.

The invention claimed is:

1. A method for processing a sample of biological material containing target cells and accompanying cells for extracting nucleic acids of the target cells, the method comprising:
   accumulating the target cells of the sample by removing the target cells or the accompanying cells from the sample;
   disrupting the target cells with ultrasonic energy, wherein an ultrasonic generator is coupled to the filter in order to generate a target-cell lysate containing the nucleic acids of the target cells; and
   purifying the nucleic acids from the target-cell lysate in order to extract the nucleic acids of the target cells, wherein:
   disrupting the target cells includes disrupting the target cells on a filter, and
   when the target cells are ultrasonically disrupted on the filter, the filter is completely or partially broken up into the filter's constituents.

2. The method as claimed in claim 1, wherein:
   accumulating the target cells includes removing the target cells from the sample by an accumulation filter.

3. The method as claimed in claim 2, wherein:
   accumulating the target cells includes cleaning the accumulation filter after removing the target cells from the sample.

4. The method as claimed in claim 1, wherein:
   accumulating the target cells includes adjusting the temperature of the sample to a lysis temperature for disrupting and predamaging the accompanying cells, and
   accumulating the target cells includes lysing the accompanying cells by chemical lysis and enzymatically digesting the nucleic acids released from the accompanying cells.

5. The method as claimed in claim 4, wherein:
   the accompanying cells are lysed and the nucleic acids released from the accompanying cells are digested before, during, or after the temperature of the sample is adjusted to a lysis temperate, and
   a viscosity of the sample is lowered when the accompanying cells are lysed and the nucleic acids released from the accompanying cells are digested.

6. The method as claimed in claim 1, further comprising:
   predisrupting the accompanying cells by a lysis buffer and/or coupling-in of ultrasound before accumulating the target cells of the sample.

7. The method as claimed in claim 1, wherein accumulating the target cells includes diluting the sample.

* * * * *